United States Patent
Brand et al.

(10) Patent No.: US 9,958,316 B2
(45) Date of Patent: May 1, 2018

(54) SYSTEM AND METHOD FOR MEASURING A RESONANCE FREQUENCY OF A TUBE

(75) Inventors: Maarten Leonardus Christian Brand, Monroeville, PA (US); Liang Dong, Shanghai (CN); Juan Du, Shanghai (CN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1765 days.

(21) Appl. No.: 13/383,875

(22) PCT Filed: Jul. 13, 2010

(86) PCT No.: PCT/IB2010/053190
§ 371 (c)(1),
(2), (4) Date: Jan. 13, 2012

(87) PCT Pub. No.: WO2011/007315
PCT Pub. Date: Jan. 20, 2011

(65) Prior Publication Data
US 2012/0116238 A1 May 10, 2012

(30) Foreign Application Priority Data

Jul. 16, 2009 (CN) .......................... 2009 1 0160418

(51) Int. Cl.
*G01H 13/00* (2006.01)
*A61B 5/08* (2006.01)
(Continued)

(52) U.S. Cl.
CPC ......... *G01H 13/00* (2013.01); *A61B 5/02007* (2013.01); *A61B 5/02133* (2013.01);
(Continued)

(58) Field of Classification Search
CPC ................ G01H 13/00; A61B 5/02007; A61B 5/02133; A61B 5/085; A61B 8/0891
See application file for complete search history.

(56) References Cited

U.S. PATENT DOCUMENTS 3,726,129 A * 4/1973 Thorne .................. G01H 13/00
374/117
6,168,568 B1 * 1/2001 Gavriely ................ A61B 5/087
600/529

(Continued)

FOREIGN PATENT DOCUMENTS

| CN | 1194368 A | 9/1998 |
|----|-----------|--------|
| JP | 61235712 | 10/1986 |

(Continued)

*Primary Examiner* — Catherine B Kuhlman
(74) *Attorney, Agent, or Firm* — Michael W. Haas

(57) ABSTRACT

The invention proposes a system for measuring a resonance frequency of a tube. The system comprises: an oscillating unit (21) for oscillating the tube at a plurality of oscillation frequencies, respectively; a detecting unit (22) for detecting a time delay of transmitting a pressure pulse from a first position to a second position in the tube when the tube is oscillated at each oscillation frequency, wherein, when the tube is oscillated at each oscillation frequency in a specific oscillation frequency range of the plurality of oscillation frequencies, the detecting unit (22) detects a variation of the time delay—a determining unit (23) for determining a maximal variation of the time delay when the tube is oscillated at the oscillation frequencies in the specific oscillation frequency range; and—an indicating unit (24) for indicating an oscillation frequency corresponding to the maximal variation of the time delay, being a resonance frequency of the tube.

12 Claims, 4 Drawing Sheets

(51) Int. Cl.
   *A61B 5/021*   (2006.01)
   *A61B 5/02*    (2006.01)
   *A61B 8/00*    (2006.01)
   *A61B 8/08*    (2006.01)

(52) U.S. Cl.
   CPC ............... *A61B 5/08* (2013.01); *A61B 8/00* (2013.01); *A61B 8/0891* (2013.01)

(56)         References Cited

U.S. PATENT DOCUMENTS

| | | |
|---|---|---|
| 6,383,142 B1 | 5/2002 | Gavriely |
| 6,443,907 B1 | 9/2002 | Mansy et al. |
| 2002/0134159 A1* | 9/2002 | He .................. G01B 17/02 73/579 |
| 2003/0094031 A1 | 5/2003 | Huang et al. |
| 2003/0220556 A1* | 11/2003 | Porat ............... A61B 5/0051 600/407 |
| 2007/0055151 A1 | 3/2007 | Shertukde et al. |
| 2007/0055175 A1 | 3/2007 | Caro |

FOREIGN PATENT DOCUMENTS

| | | |
|---|---|---|
| JP | 06037574 | 2/1994 |
| JP | 2003530940 A | 10/2003 |
| JP | 2004512066 A | 4/2004 |
| WO | 9949778 | 10/1999 |
| WO | 0180741 | 11/2001 |
| WO | WO0180741 A1 | 11/2001 |
| WO | WO0230280 A1 | 4/2002 |
| WO | 2006099670 | 9/2006 |

\* cited by examiner

SYSTEM AND METHOD FOR MEASURING A RESONANCE FREQUENCY OF A TUBE

FIELD OF THE INVENTION

The invention relates to a system for, and method of, measuring properties of a tube, particularly to a system for, and method of, measuring a resonance frequency of a tube.

BACKGROUND OF THE INVENTION

In a human body or an animal body, the most notable flexible tubes are blood vessels and airways. The airways may comprise trachea, main bronchi, small bronchiole, etc. In the medical diagnostic area, it is useful to know the response of a tube to an excitation. The excitation can be a natural excitation, such as a contraction of a heart, or an artificial excitation. The artificial excitation can be a pressure excitation from an external body. The response of a tube to an excitation can be used for diagnosis of pathologies or used for optimizing therapeutic treatment.

The response of a tube to an excitation can result in resonance. Resonance occurs when an external excitation leads to maximum energy storage in a tube and causes the maximal amplitude of the movements of the tube wall. The resonance of a tube relates to the movements caused by the excitation applied to a tube. The frequency at which resonance occurs is dependent, among other factors, on material properties of the tube. For diagnosis purposes, measuring the movement of a tube caused by an excitation is already practiced.

For example, arterial stiffness measurements are often based on measuring the time delay of a pressure pulse travelling from a position to another position along the artery. The time delay depends on the velocity of a pressure pulse travelling in the artery, and the time delay is correlated to the elasticity of the artery wall. Currently, the method of detecting the resonance frequency of an artery is to take out a segment of an artery of an animal, to apply a pressure pulse to excite the segment of the artery, and to measure the amplitude of the tube wall movements, which leads to an observation of resonance. When people notice that the segment of the artery is resonant, the frequency corresponding to the resonance is a resonance frequency of the artery. However, the current method is not useful for clinical practice, since the arteries are in the human body or animal body, so in normal clinical practice, people cannot see whether the arteries are resonant, which makes it difficult to determine a resonance frequency for the arteries based on the current method.

Another example is to measure the properties of airways, e.g. trachea, main bronchi, or small bronchioles, so as to measure the resonance frequency of airways for assisting cough by optimizing the treatment frequency when oscillation/percussion treatment is used, or to aid in diagnosis or disease management. A resonance frequency is an optimal oscillation frequency to help a patient to enhance mucus expectoration.

Currently, Forced Oscillation Technology (FOT) and Impulse Oscillometry (IOS) are used to measure air pressure and airflow at a mouth in response to periodical pressure variations and pressure pulses, respectively, caused by pressure applied to a lung system, in order to diagnose pathologies. Based on FOT and IOS, a resonance frequency is determined when there is no phase delay between the applied pressure pulse and the detected response at the mouth. However, the resonance frequency determined by FOT or IOS is limited to low frequencies due to the inherent inaccuracy of the system.

Furthermore, to improve lung mucus expectoration, normally, patients are instructed to cough in different ways, so as to first move mucus from the smaller bronchioles to the main bronchi, then to move mucus from the main bronchi to the trachea, and finally to cough mucus up. Thus, it is necessary to detect resonances for the smaller bronchioles, the main bronchi, and the trachea separately. Especially, some diseases only have an impact on part of the whole lung system. For example, COPD (Chronic Obstructive Pulmonary Disease) mainly has an effect on the small bronchioles, which shows a necessity to identify independently the resonance of the smaller airways of a lung system for diagnosing COPD. But, currently, based on FOT or IOS, it is difficult to distinguish resonances of the small bronchioles, the main bronchi, and trachea of a lung system separately.

SUMMARY OF THE INVENTION

An object of this invention is to propose a system for accurately measuring a resonance frequency of a tube.

A system for measuring a resonance frequency of a tube comprises:
  an oscillating unit for respectively oscillating the tube at a plurality of oscillation frequencies
  a detecting unit for detecting a time delay of transmitting a pressure pulse from a first position to a second position in the tube when the tube is oscillated at each oscillation frequency, wherein, when the tube is oscillated at each oscillation frequency in a specific oscillation frequency range of the plurality of oscillation frequencies, the detecting unit detects a variation of the time delay;
  a determining unit for determining a maximal variation of the time delay when the tube is oscillated at the oscillation frequencies in the specific oscillation frequency range;
  and
  an indicating unit for indicating an oscillation frequency corresponding to the maximal variation of the time delay, being a resonance frequency of the tube.

The advantage is that the system can more accurately measure a resonance frequency of a tube.

In an embodiment, the system comprises a comparing unit for comparing the resonance frequency with a pre-defined frequency table to determine a property/a set of properties of the tube.

The advantage is that a more accurate property/a set of more accurate properties of a tube can be measured based on the accurate resonance frequency.

In another embodiment, the system comprises a calculating unit for calculating a property/a set of properties of the tube based on the resonance frequency.

The advantage is that a more accurate property/a set of more accurate properties of a tube can be calculated based on the accurate resonance frequency.

In a further embodiment, the system comprises an assisting unit for assisting cough based on the resonance frequency, if the tube is an airway.

The advantage is that a cough can be realized more effectively based on the accurate resonance frequency.

The invention further proposes a system for measuring at least one resonance frequency of a tube, and the system comprises:

an oscillating unit for oscillating the tube at a plurality of oscillation frequencies, respectively;

a detecting unit for detecting a time delay of transmitting a pressure pulse from a first position to a second position in the tube, when the tube is oscillated at each oscillation frequency;

and an indicating unit for outputting a graph to reflect a correlation between the plurality of oscillation frequencies and the time delays, wherein, in at least one specific oscillation frequency range of the plurality of oscillation frequencies, each oscillation frequency corresponds to a variation of the time delay, and, in the at least one specific oscillation frequency range, an oscillation frequency corresponding to a maximal variation of the time delay, being the at least one resonance frequency of the tube.

The advantage is that the system can more accurately generate a graph to show at least one resonance frequency of a tube.

The invention also proposes a method corresponding to the system of measuring a resonance frequency of a tube.

Detailed explanations and other aspects of the invention will be given below.

DESCRIPTION OF THE DRAWINGS

The above and other objects and features of the present invention will become more apparent from the following detailed description considered in connection with the accompanying drawings, in which.

The same reference numerals are used to denote similar parts throughout the figures.

DETAILED DESCRIPTION

A velocity of transmitting a pressure pulse in a tube correlates to the properties of the tube wall, the properties of the content (e.g. gas/liquid) in the tube, the diameter of the tube, and an external oscillation pressure which causes a variation of the diameter of the tube.

For example, the velocity of transmitting a pressure pulse in a blood vessel correlates to the compliance of the blood vessel wall, the density of blood in the blood vessel, the diameter of the blood vessel, and an external oscillation pressure. An external oscillation pressure causes the blood vessel wall to vibrate with positive divergence and negative divergence, so as to cause the diameter of the blood vessel to increase and decrease in a cyclic pattern. A velocity variation of a pressure pulse in the blood vessel happens based on the diameter variation of the blood vessel. The velocity variation of a pressure pulse in a blood vessel causes a time variation of transmitting a pressure pulse from a position to another position along the blood vessel. The external oscillation pressure is transmitted to a blood vessel wall and blood through corresponding skin covering the blood vessel.

In another example, the velocity of transmitting a pressure pulse in an airway of a lung correlates to the diameter of the tube, the density of air contained in the airway, the compliance of the airway, and the external oscillation pressure applied to the airway. When an airway is oscillated at an oscillation pressure, the airway expands and contracts in a cyclic pattern and the diameter of the airway also varies in a cyclic pattern. The velocity of a pressure pulse in the airway varies based on the variation of the diameter, and the velocity variation causes time variation of transmitting a pressure pulse from a position to another position along the airway.

Figure 1A:
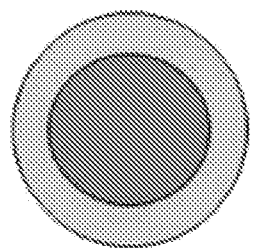
FIG. 1A depicts a cross section of a tube without being oscillated.
Figure 1B:
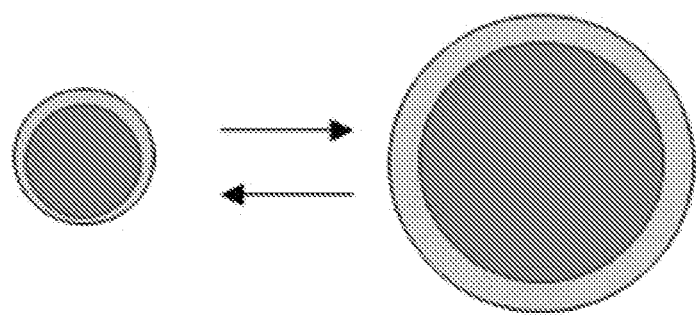
FIG. 1B depicts a periodical variation from the smallest diameter to the biggest diameter of a tube being oscillated.

FIG. 1A depicts a cross section of a tube without being oscillated, and FIG. 1B depicts a periodic variation from a smallest diameter to a largest diameter of a tube being oscillated. The diameter of the tube varies periodically, which causes the velocity of a pressure pulse in the tube to vary periodically. As shown in FIG. 1B, when the diameter of the tube is maximal, the velocity of transmitting the pressure pulse is maximal, and when the diameter of the tube is minimal, the velocity of transmitting the pressure pulse is minimal. The maximal variation of the velocity is caused by the oscillation pressure, and a corresponding frequency of the oscillation pressure is a resonance frequency of the tube.

A time delay is the time of transmitting a pressure pulse from a first position to a second position along a tube, and the time delay correlates to the velocity of the pressure pulse in the tube. If the velocity of the pressure pulse in the tube varies, the time delay also varies. If the variation of the velocity is maximal, the variation of the time delay is maximal, so the maximal variation of the time delay also indicates a resonance of a tube.

Figure 2:
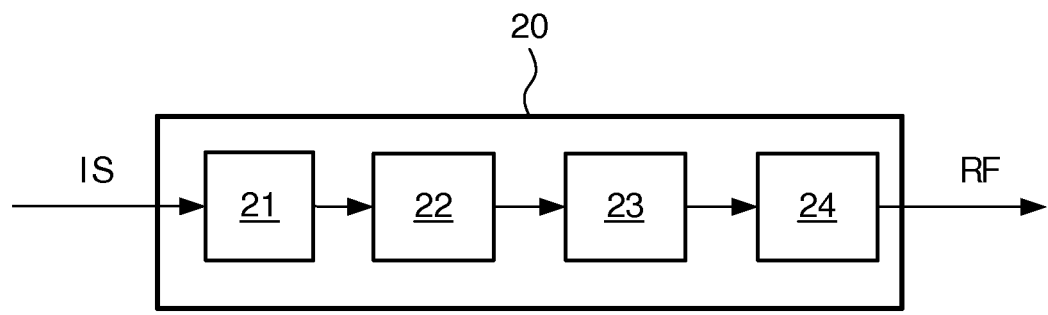
FIG. 2 schematically shows a system for measuring a resonance frequency of a tube according to an embodiment of the invention.

FIG. 2 schematically shows a system for measuring a resonance frequency of a tube according to an embodiment of the invention. The system 20 comprises:

an oscillating unit 21 for oscillating the tube at a plurality of oscillation frequencies, respectively;

a detecting unit 22 for detecting a time delay of transmitting a pressure pulse from a first position to a second position in the tube when the tube is oscillated at each oscillation frequency, wherein, when the tube is oscillated at each oscillation frequency in a specific oscillation frequency range of the plurality of oscillation frequencies, the detecting unit detects a variation of the time delay;

a determining unit 23 for determining a maximal variation of the time delay when the tube is oscillated at the oscillation frequencies in the specific oscillation frequency range;

and an indicating unit 24 for indicating an oscillation frequency corresponding to the maximal variation of the time delay, being a resonance frequency of the tube.

The tube is a flexible tube, such as a blood vessel or an airway of a lung system. The airway can be a trachea, a main bronchus, or a small bronchiole. Based on the oscillation frequencies, the tube wall is oscillated. The tube contains content, such as a gas or a liquid. The pressure pulse may be caused by an excitation provided by an exciting unit (not shown in FIG. 2), if the tube is an airway. The pressure pulse may be caused by a contraction of a heart, if the tube is a blood vessel.

After receiving an instruction signal (shown as IS in FIG. 2), the oscillating unit 21 starts to generate a plurality of oscillation pressures to oscillate the tube one by one, and each oscillation pressure corresponds to a different oscillation frequency. The instruction signal can be inputted by a user (a doctor, a patient, etc.).

The plurality of oscillation frequencies are in a pre-defined frequency range, and the pre-defined frequency range may be provided by a manufacturer of the system 20 or a user (a doctor, a patient, etc.). If the pre-defined frequency range is not stored in the system 20, a user may input oscillating frequencies of the pre-defined range to the oscillating unit 20 for oscillating the tube respectively. If the pre-defined frequency range is stored in system 20, a user and/or the oscillating unit 21 can select oscillation frequencies from the pre-defined frequency range to oscillate the tube respectively. The pre-defined oscillation frequency range may be a range of 1 Hz to 500 Hz, 1 Hz to 100 Hz, etc.

The first position of the tube can be a position along the transmitting direction of the pressure pulse in the tube, and the second position of the tube is another position along the transmitting direction of the pressure pulse from the first position of the tube. The time at which the pressure pulse arrives at the first position is represented by a first arriving time (called FAT in the following) and the time of the pressure pulse arriving at the second position is represented by a second arriving time (called SAT in the following). The detecting unit 22 comprises two sensors to collect the FAT of the first position and the SAT of the second position, respectively. The sensors can be microphones.

Alternatively, if the tube is an airway and the pressure pulse is caused by the exciting unit, the first position of the tube can be the position located at the exciting unit, and the second position of the tube is another position along the transmitting direction of the pressure pulse in the tube. The detecting unit 22 comprises a sensor to collect the SAT of the second position, and the FAT of the first position is almost 0. The sensor can be a microphone.

The detecting unit 22 is intended to calculate the time delay (time difference) of transmitting the pressure pulse from the first position to the second position based on the FAT of the first position and the SAT of the second position.

The indicating unit 24 is intended to indicate the resonance frequency (shown as RF in FIG. 2) by character information, a graph, a light, a voice, a warning, etc. The indicating unit 24 may also be intended to indicate to store the resonance frequency in a memory, and the memory can be in the system 20 or in an external device.

For a medical diagnostic application, the system 20 may comprise a comparing unit (not shown in FIG. 2) for comparing the resonance frequency with a pre-defined resonance frequency table to determine a property/a set of properties of the tube. The property can be a mechanical property of a blood vessel or a lung system, such as the elasticity of a tube wall. The pre-defined frequency table may comprise a set of resonance frequencies, wherein each resonance frequency may correspond to a status of the human body or the animal body and each resonance frequency may also correspond to a property or a set of properties of the tube.

For another medical diagnostic application, the system 20 may comprise a calculating unit (not shown in FIG. 2) for calculating a property/a set of properties of the tube based on the resonance frequency. The correlation between a resonance frequency of a blood vessel and the elasticity of the blood vessel can be represented by the following known equation:

$$f=\sqrt{E/(3\rho)}/(2\pi R)$$

In the equation, f represents the resonance frequency, E represents the elasticity of the blood vessel wall, ρ represents the density of the blood in the blood vessel, and R is the inner radius of the blood vessel. Based on the equation and the resonance frequency, the elasticity of the blood vessel can be calculated, since, if assuming a relatively constant density of the blood, the resonance frequency is directly related to the elasticity of the blood vessel wall.

For a further medical diagnostic application, the system 20 may also further comprise an assisting unit for assisting a lung system to cough based on the resonance frequency, if the tube is an airway. For example, the resonance frequency is used to oscillate a bronchus of the lung system to help the lung system to cough. The assisting unit can be combined with a Positive Expiratory Pressure (PEP) therapy device.

The plurality of oscillation frequencies may comprise a set of specific oscillation frequency ranges. In the set of specific oscillation frequency ranges, when each oscillation frequency is used to oscillate the tube, the time delay of transmitting the pressure pulse from the first position to the second position in the tube varies. A maximal variation of the time delay is included and corresponds to an oscillation frequency in each specific oscillation range. The detecting unit 22 may be intended to detect the variation of the time delay when each oscillation frequency in the set of oscillation frequency ranges is used to oscillate the tube. The determining unit 23 may be intended to detect a maximal variation of the time delay, when the oscillation frequencies in each set of specific oscillation frequency ranges are used for oscillating the tube, thus a set of maximal variations of the time delay are determined corresponding to the set of specific oscillation frequency ranges, respectively. The indicating unit 24 may be intended to indicate the oscillation frequency that corresponds to each maximal variation of the time delay, being a resonance frequency of the tube, so that a set of resonance frequencies of the tube is indicated.

Alternatively, the comparing unit may compare the set of resonance frequencies with a pre-defined resonance frequency table to determine a property/a set of properties of the tube. The calculating unit may calculate a property/a set of properties of the tube based on the set of resonance frequencies. The assisting unit may be used for assisting a lung system to cough based on the set of resonance frequencies, for example selecting a resonance frequency that corresponds to the largest one of the maximal variations of the time delay, to assist cough.

The resonance frequencies of airways, e.g. trachea, main bronchi, and small bronchioles are different. Based on the mentioned embodiment of the invention, the resonance frequency of different airways can be measured separately. For example, the resonance frequencies of trachea, main bronchi, and small bronchioles can be applied to trachea, main bronchi, and small bronchioles, respectively, to assist cough.

Figure 3:
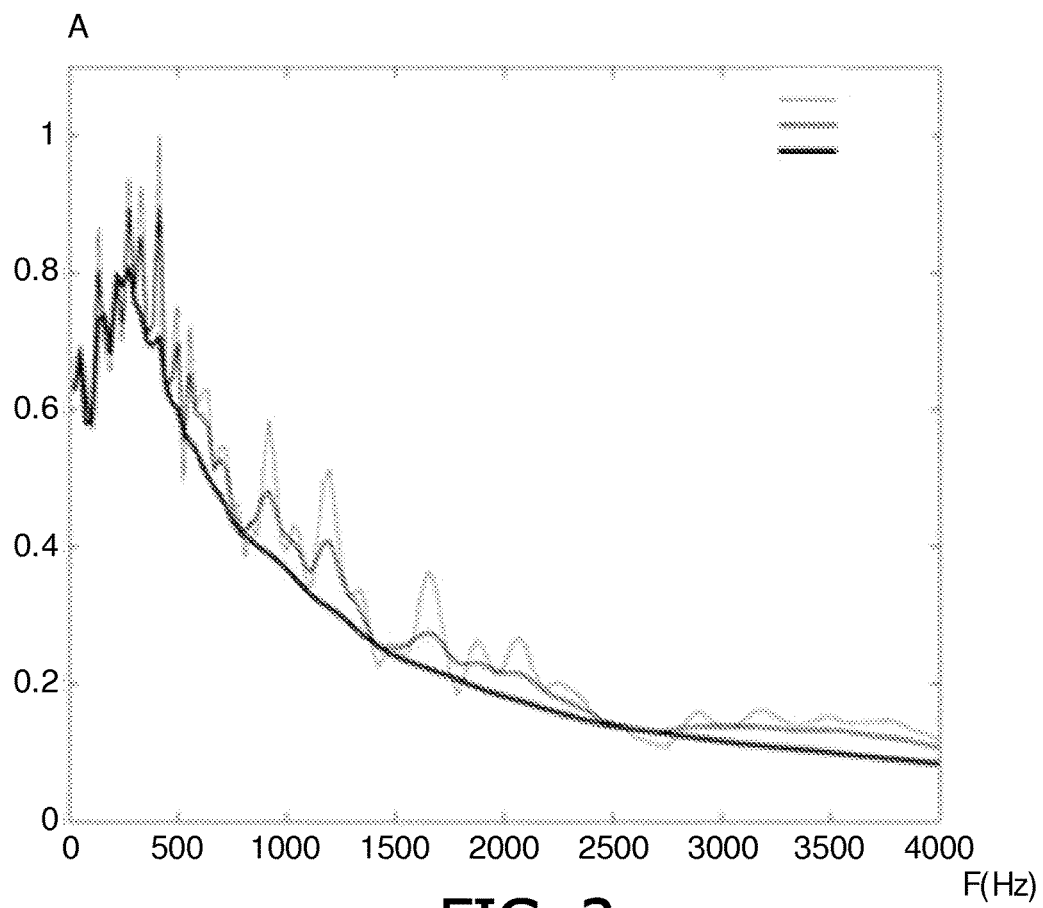
FIG. 3 is a diagram illustrating a correlation between oscillation frequency and amplitude.

FIG. 3 is a diagram illustrating a correlation between oscillation frequency (shown as F) and amplitude (shown as A). In FIG. 3, a plurality of oscillating frequencies are applied on three tubes and causes three sets of maximal (peak) oscillating amplitudes for the three tubes, respectively. The oscillation frequency having the maximal amplitude is a resonance frequency. A maximal amplitude of the tube wall causes a maximal variation of velocity of the pressure pulse in the tube, and therefore causes a maximal variation of the time delay of transmitting the pressure pulse from the first position to the second position in the tube.

In another embodiment, the indicating unit (24) of the system 20 is further used to output a graph to reflect a correlation between the plurality of oscillation frequencies and the time delays, wherein, in at least one specific oscillation frequency range of the plurality of oscillation frequencies, each oscillation frequency corresponds to a variation of the time delay, and, in the at least one specific oscillation frequency range, the oscillation frequency corresponding to a maximal variation of the time delay is the at least one resonance frequency of the tube.

Figure 4:
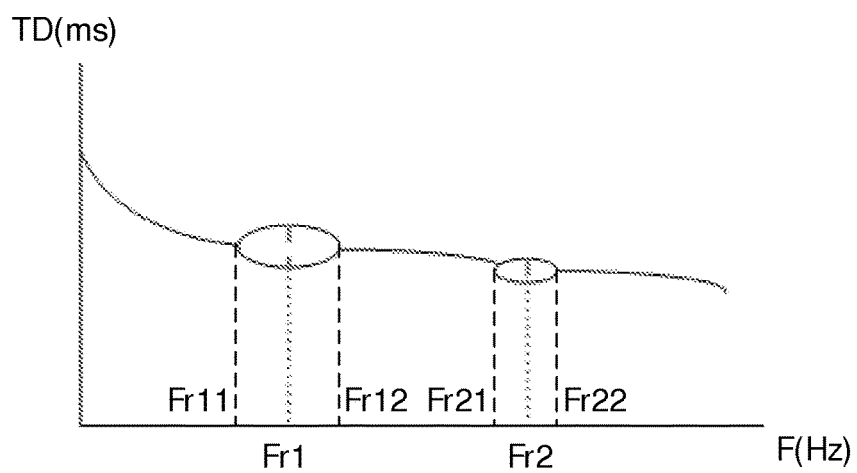
FIG. 4 schematically shows a correlation between the time delay and the oscillation frequency.

FIG. 4 schematically shows a correlation between the time delay (shown as TD) and the oscillation frequency (shown as F). Each resonance frequency corresponds to a maximal variation of the time delay, e.g. Fr1 corresponds to a maximal variation of the time delay in a specific oscillation frequency range Fr11 to Fr12 and Fr2 corresponds to a maximal variation of the time delay in another specific oscillation frequency range Fr21 to Fr22. In FIG. 4, the maximal variation corresponding to Fr1 is the largest one. The unit of the oscillation frequency is Hz and the unit of the time delay is ms (millisecond). When the tube is oscillated at an oscillation frequency, the corresponding time delay is detected several times to check whether the time delay varies.

Figure 5:
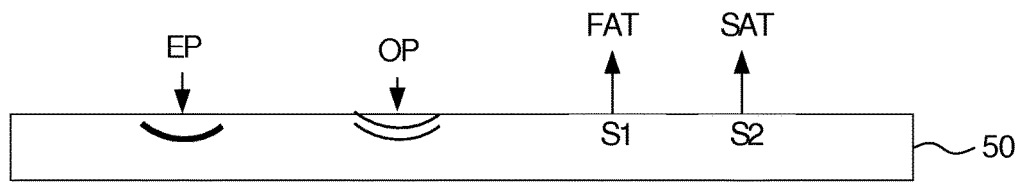
FIG. 5 schematically shows an example of measuring a resonance frequency of a tube.

FIG. 5 schematically shows an example of measuring a resonance frequency of a tube. The tube 50 is excited by an excitation pressure (shown as EP in FIG. 5) to cause a pressure pulse to be transmitted in the tube 50. An oscillation pressure (shown as OP in FIG. 5) is applied to the tube 50 for causing the tube 50 to oscillate. The sensor S1 is used to collect the FAT of the first position and the sensor S2 is used to collect the SAT of the second position, so as to get the time delay between the first position and the second position based on FAT and SAT. The excitation pressure is provided by the exciting unit and the oscillation pressure is provided by the oscillating unit 21.

Figure 6:
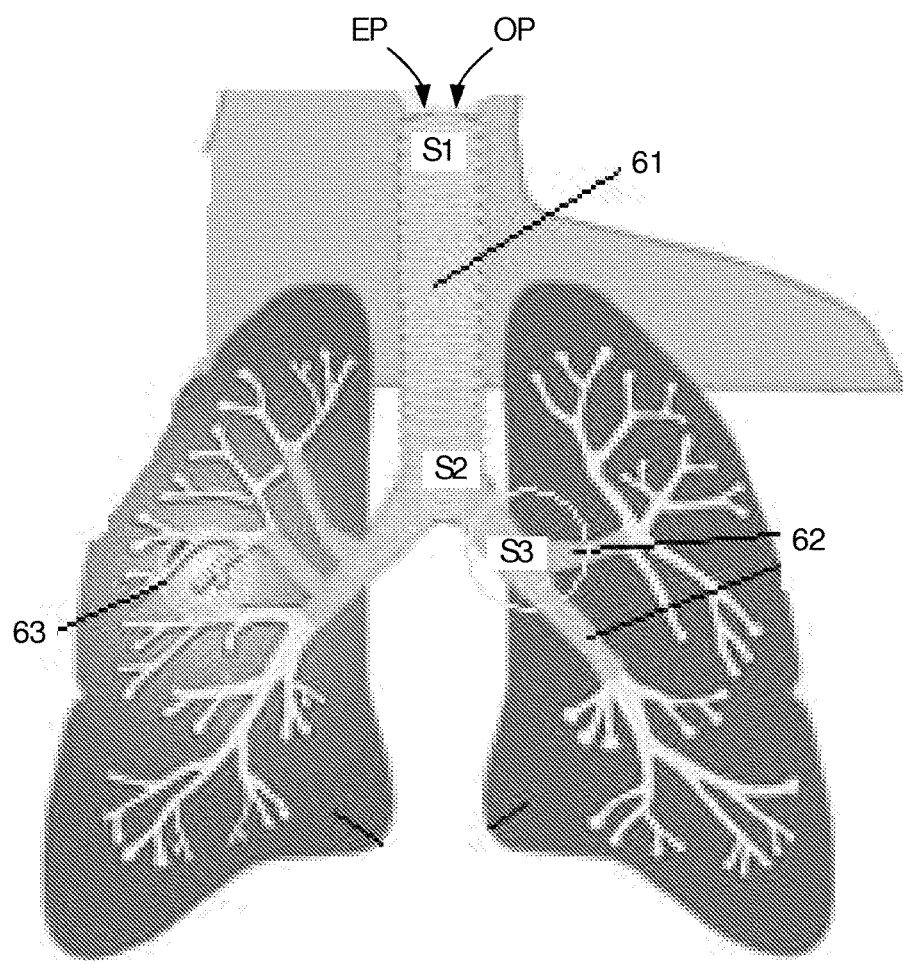
FIG. 6 schematically shows another example of measuring a resonance frequency of a tube.

FIG. 6 schematically shows another example of measuring a resonance frequency of a tube. In an embodiment, a lung system is given, and the lung system comprises several airways, such as a trachea 61, main bronchi 62, and small bronchioles 63. The excitation pressure (shown as EP in FIG. 6) is applied to the trachea 61 through a mouth (not shown in FIG. 6), which causes a pressure pulse to be transmitted from trachea, via main bronchi, to small bronchioles, and the oscillation pressure (shown as OP in FIG. 6) is applied to cause the airways oscillating. The resonance frequencies of trachea 61, main bronchi 62, and bronchioles 63 can be measured separately, wherein sensors S1 and S2 are used to measure the resonance frequency of trachea 61 and sensors S2 and S3 are used to measure the resonance frequency of a main bronchus 62. The excitation pressure is provided by the exciting unit and the oscillation pressure is provided by the oscillating unit 21. The state of the lung system (in exhaled state or not in exhaled state) may influence the transmission of the pressure pulse, so the lung system is to be kept at an identical state, for example fully inhaled state, for a short time, to complete the measuring of resonance frequencies of the lung system. The system 20 may further comprise a device for ensuring that the measurements are made at different lung volumes in order to ensure all airways can be measured.

Figure 7:
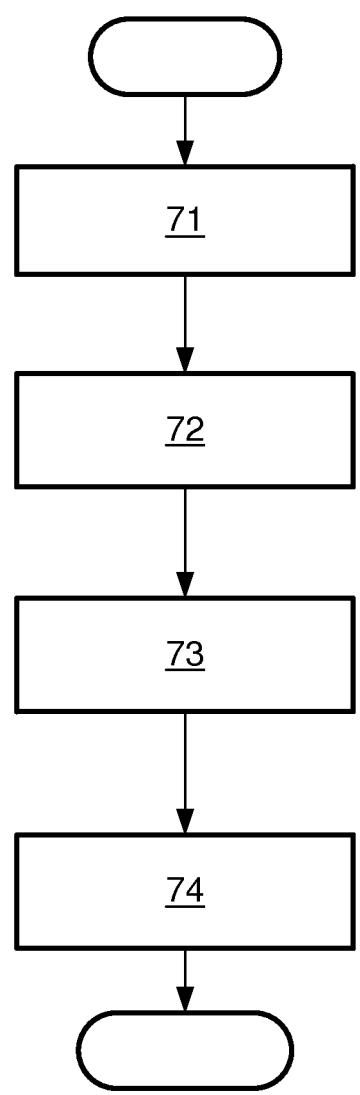
FIG. 7 schematically depicts a method for measuring a resonance frequency of a tube according to an embodiment of the invention.

FIG. 7 schematically depicts a method of measuring a resonance frequency of a tube. The method comprises the following the steps.

A step 71 is to oscillate the tube at a plurality of oscillation frequencies, respectively. The oscillation frequency is in a pre-defined frequency range and the pre-defined frequency range may be provided by a manufacturer of the system 20 or by a user.

A step 72 is to detect a time delay of transmitting a pressure pulse from a first position to a second position in the tube when the tube is oscillated at each oscillation frequency, wherein, when the tube is oscillated at each oscillation frequency in a specific oscillation frequency range of the plurality of oscillation frequencies, the detecting step 72 detects a variation of the time delay. The pressure pulse may be caused by a contraction of a heart, if the tube is a blood vessel.

A step 73 is to determine a maximal variation of the time delay when the tube is oscillated at the oscillation frequencies in the specific oscillation frequency range.

A step 74 is to indicate the oscillation frequency corresponding to the maximal variation of the time delay, being a resonance frequency of the tube.

The indicating step 74 is intended to indicate the resonance frequency by character information, a graph, a light, a voice, a warning, etc. The indicating step 74 may also be intended to indicate to store the resonance frequency in a memory.

For a medical diagnostic application, the method may comprise a step of comparing the resonance frequency with a pre-defined resonance frequency table to determine a property/a set of properties of the tube.

For another medical diagnostic application, the method may comprise a step of calculating a property/a set of properties of the tube based on the resonance frequency.

For a further medical diagnostic application, the method may also further comprise a step of assisting a lung system to cough based on the resonance frequency, if the tube is an airway.

The plurality of oscillation frequencies may comprise a set of specific oscillation frequency ranges. In the set of specific oscillation frequency ranges, when each oscillation frequency is used to oscillate the tube, the time delay of transmitting the pressure pulse from the first position to the second position in the tube varies. A maximal variation of the time delay is included and corresponds to an oscillation frequency in each specific oscillation range. The detecting step 72 may be intended to detect the variation of the time delay when each oscillation frequency in the set of oscillation frequency ranges is used to oscillate the tube. The determining step 73 may be intended to detect a maximal variation of the time delay, when the oscillation frequencies in each set of specific oscillation frequency ranges are used for oscillating the tube, thus a set of maximal variations of the time delay are determined corresponding to the set of specific oscillation frequency ranges, respectively. The indicating step 74 may be intended to indicate that the oscillation frequency that corresponds to each maximal variation of the time delay, being a resonance frequency of the tube, and then indicate a set of resonance frequencies of the tube.

Alternatively, a comparing step may compare the set of resonance frequencies with a pre-defined resonance frequency table to determine a property/a set of properties of the tube. A calculating step may calculate a property/a set of properties of the tube based on the set of resonance frequencies. An assisting step may be used for assisting a lung system to cough, based on the set of resonance frequencies, for example selecting a resonance frequency that corresponds to the largest one of the maximal variations of the time delay, to assist cough.

In another embodiment, the indicating step 74 is further intended to output a graph to reflect a correlation between the plurality of oscillation frequencies and the time delays, wherein, in at least one specific oscillation frequency range of the plurality of oscillation frequencies, each oscillation frequency corresponds to a variation of the time delay, and, in the at least one specific oscillation frequency range, the oscillation frequency corresponding to a maximal variation of the time delay is the at least one resonance frequency of the tube.

A computer program is used in the method of measuring a resonance frequency of a tube.

It should be noted that the abovementioned embodiments illustrate rather than limit the invention and that those skilled in the art will be able to design alternative embodiments without departing from the scope of the appended claims. In the claims, any reference signs placed between parentheses shall not be construed as limiting the claim. The word "comprising" does not exclude the presence of elements or steps not listed in a claim or in the description. The word "a" or "an" preceding an element does not exclude the presence of a plurality of such elements. The invention can be implemented by a unit of hardware comprising several distinct elements and by a unit of a programmed computer. In the system claims enumerating several units, several of these units can be embodied by one and the same item of hardware or software. The usage of the words first, second, third, et cetera, does not indicate any ordering. These words are to be interpreted as names.

The invention claimed is:

1. A system for measuring a resonance frequency of a tube, the system comprising:
    a computer system programmed by computer-readable instructions that, when executed, cause the computer system to:
    oscillate the tube at a plurality of oscillation frequencies;
    detect, while the tube oscillates at an individual frequency, a time delay of transmitting a pressure pulse from a first position to a second position in the tube, wherein, when the tube is oscillated at different oscillation frequencies in a specific oscillation frequency range of the plurality of oscillation frequencies, detecting the time delay of transmitting a pressure pulse further comprises detecting a variation of the time delay at each of the different oscillation frequencies;
    determine a maximal variation of the time delay when the tube is oscillated at the different oscillation frequencies in the specific oscillation frequency range; and
    indicate an oscillation frequency corresponding to the maximal variation of the time delay, the oscillation frequency corresponding to the maximal variation of the time delay being a resonance frequency of the tube.

2. The system as claimed in claim 1, wherein the computer system is further caused to compare the resonance frequency with a pre-defined frequency table to determine one or both of a property or a set of properties of the tube.

3. The system as claimed in claim 1, wherein the computer system is further caused to calculate one or both of a property or a set of properties of the tube based on the resonance frequency.

4. The system as claimed in claim 1, wherein the tube is an airway, and wherein the computer system is further caused to use the resonance frequency to oscillate the airway for assisting a cough.

5. The system as claimed in claim 1, wherein the tube is an airway, and wherein the computer system is further caused to excite the tube to generate the pressure pulse.

6. The system as claimed in claim 1, wherein the tube is a blood vessel and wherein the pressure pulse is generated by contraction of a heart.

7. The system as claimed in claim 1, wherein the computer system is caused to indicate the resonance frequency by character information, a graph, a light, a voice, or a warning, or to store the resonance frequency in a memory.

8. A method of assisting a cough based on a resonance frequency of a tube, the method comprising the steps of:
    oscillating, via an oscillator, the tube at a plurality of oscillation frequencies;
    detecting, via one or more sensors, a time delay of transmitting a pressure pulse from a first position to a second position in the tube while the tube oscillates at an individual frequency of the plurality of oscillation frequencies, wherein, when the tube is oscillated at different oscillation frequencies in a specific oscillation frequency range of the plurality of oscillation frequencies, the detecting step includes detecting a variation of the time delay at each of the different oscillation frequencies;
    determining, via a computer, a maximal variation of the time delay when the tube is oscillated at the different oscillation frequencies in the specific oscillation frequency range;
    indicating, via the computer, an oscillation frequency corresponding to the maximal variation of the time delay, the oscillation frequency corresponding to the maximal variation of the time delay being a resonance frequency of the tube; and
    assisting, via the computer, a cough based on the resonance frequency of the tube.

9. The method as claimed in claim 8, further comprising a step of comparing the resonance frequency with a pre-defined frequency table to determine one or both of a property or a set of properties of the tube.

10. The method as claimed in claim 8, further comprising a step of calculating one or both of a property or a set of properties of the tube based on the resonance frequency.

11. The method as claimed in claim 8, wherein the tube is an airway, wherein assisting the cough comprises using the resonance frequency to oscillate the airway.

12. The method as claimed in claim 8, wherein the tube is an airway, the method further comprising a step of exciting the tube to generate the pressure pulse.

* * * * *